United States Patent [19]

Geist et al.

[11] Patent Number: 4,889,612

[45] Date of Patent: Dec. 26, 1989

[54] ION-SELECTIVE ELECTRODE HAVING A NON-METAL SENSING ELEMENT

[75] Inventors: Jill M. Geist, Wildwood; Scott C. Messner; Thomas G. Schapira, both of Lindenhurst, all of Ill.

[73] Assignee: Abbott Laboratories, North Chicago, Ill.

[21] Appl. No.: 53,446

[22] Filed: May 22, 1987

[51] Int. Cl.[4] ............................................. G01N 27/30
[52] U.S. Cl. ..................................... 204/416; 204/418; 357/25; 357/22
[58] Field of Search ........................ 204/416, 418, 419; 357/22 B, 25

[56] References Cited

U.S. PATENT DOCUMENTS

| | | | |
|---|---|---|---|
| 3,926,764 | 12/1975 | Ruzicka et al. | 204/195 F |
| 4,020,830 | 5/1977 | Johnson et al. | 204/195 M |
| 4,053,381 | 11/1977 | Hamblen et al. | 204/195 M |
| 4,133,735 | 1/1979 | Afromowitz et al. | 204/195 G |
| 4,180,771 | 12/1979 | Guckel | 204/195 M |
| 4,184,936 | 1/1980 | Paul et al. | 204/195 R |
| 4,214,968 | 7/1980 | Battaglia et al. | 204/195 M |
| 4,225,410 | 9/1980 | Pace | 204/1 T |
| 4,269,682 | 5/1981 | Yano et al. | 204/418 |
| 4,272,328 | 6/1981 | Kim et al. | 204/1 T |
| 4,273,639 | 6/1981 | Gottermeier | 204/195 R |
| 4,276,141 | 6/1981 | Hawkins | 204/1 T |
| 4,437,969 | 3/1984 | Covington et al. | 357/25 |
| 4,393,130 | 7/1983 | Ho et al. | 430/313 |
| 4,397,714 | 8/1983 | Janata et al. | 204/1 T |
| 4,431,508 | 2/1984 | Brown, Jr. et al. | 204/418 |
| 4,449,011 | 5/1984 | Kratochvil et al. | 174/52 PE |
| 4,454,007 | 6/1984 | Pace | 204/1 T |
| 4,456,522 | 6/1984 | Blackburn | 204/416 |
| 4,486,292 | 12/1984 | Blackburn | 204/416 |
| 4,528,085 | 7/1985 | Kitajima et al. | 204/416 |
| 4,549,951 | 10/1985 | Knudson et al. | 204/416 |
| 4,683,048 | 7/1987 | Yamada et al. | 204/416 |

FOREIGN PATENT DOCUMENTS

| | | | |
|---|---|---|---|
| 0126426 | 11/1984 | European Pat. Off. | 204/418 |
| 0033483 | 11/1983 | Israel . | |

Primary Examiner—John F. Niebling
Assistant Examiner—Kathyrn Gorgos
Attorney, Agent, or Firm—Donald L. Corngelio; Martin J. Hirsch; Daniel W. Collins

[57] ABSTRACT

An ion-selective electrode having an electrically insulating substrate with a substantially planar first surface, and having a non-metallic conductor for sensing a potential affixed to the first surface beneath an ion-sensitive membrane. An electrically insulating layer covers at least a portion of the non-metallic conductor and means for making electrical contact with the non-metallic conductor.

8 Claims, 6 Drawing Sheets

ION-SELECTIVE ELECTRODE HAVING A NON-METAL SENSING ELEMENT

BACKGROUND OF THE INVENTION

The present invention pertains in general to ion-selective electrodes and in particular to planar, ion-selective electrodes having non-metallic conductor patterns.

When placed in contact with a solution, ion-selective electrodes provide an electrical output which is a function of the concentration of a particular ion in the solution. In such electrodes an output potential ("Y") is measured between a "sensing element, responsive to the concentration of the particular ion, and a "reference element," held at a constant potential, Y may be plotted against the base 10 logarithm of the concentration of the ion ("X") as a straight line having a slope ("M") and y-axis intercept ("B") as expressed in the Nernst equation:

$$Y = M(\log_{10} X) + B$$

Ion-selective electrodes conventionally have an internal reference element of Ag/AgCl immersed in a solution or gel of chloride ion. The chloride ion solution or gel holds the reference element at a constant potential, providing that the chloride concentration and thermodynamic parameters, such as temperature and pressure, are held constant. An ion-selective glass or membrane sensing element is placed in contact with the solution or gel to form an interface between test solution and this internal filling solution. However, this conventional design is complex to manufacture and difficult to miniaturize.

Two alternative configurations, chemical field effect transistors (ChemFETs) and coated wire ion-selective electrodes, have a simplified processing design. Nevertheless, these configurations do not reproduce the low drift characteristics of the conventional design. Also, neither configuration is an improvement upon the interface (i.e. membrane-gel/liquid interface) which is inherently better in the conventional design. The conventional ion-selective electrode approach, which employs an internal reference element bathed in an ionic solution or gel, is still the design of choice for most ion-selective electrode applications.

Another alternative configuration employs a graphite rod rendered hydrophobic by such materials as oil, paraffin, a silanizing agent or Teflon ®, a calomel paste rubbed into the graphite surface as a reference element, and an ion-sensitive membrane. Ruzicka et al., U.S. Pat. No. 3,926,764; and Brown et al., U.S. Pat. No. 4,431,508. The design is difficult to process or miniaturize due to a reliance upon the use of carbon rods.

Yet another ion-selective electrode is formed by mounting a cylindrical graphite plug having a first flat surface co-planar with the surface of an insulating substrate and having a second flat surface with a conductive layer which connects to the graphite plug, which passes through the substrate. Knudson et al., U.S. Pat. No. 4,549,951. The first surface of the graphite is completely covered by an electroactive membrane. This electrode is also difficult to miniaturize due to the use of a carbon rod.

In Israel Patent Application No. 33483, assigned to Hydronautics Israel Limited, a conductor covered by an ion-specific membrane at the end of an ion-specific probe may be formed of a compacted graphite powder. However, the use of a compacted powder does not suggest a readily miniaturized structure nor does any electrode in which a metallic conductor positioned directly beneath a membrane/carbon interface, such as the electrodes found in Hydronautics Israel and Knudson et al., provide a solution to the problem of leakage leading to corrosion of the metal conductor and posioning or drift resulting from such corrosion.

In an attempt at miniaturization of a graphite-containing ion-selective electrode, a plug of conductive carbon, in particular a plug of compressed graphite is embedded in a first surface of an electrically insulating cap and is separated from a solution to be tested by an hydrophobic material including a ligand capable of selective metal complexation, such as ion selective antibiotics, macrocyclics, open chain neutral or ionic ligands, certain inorganic compounds and mixtures thereof. Hawkins, U.S. Pat. No. 4,276,141. However, the need for placement of a plug directly over and of an electrical conductor passing through the cap limits both the ease with which such a device may be manufactured and the variety of configurations attainable, e.g. the number and type of electrodes per unit of surface area.

In order to achieve greater flexibility and to promote ease of miniaturization, a carbon layer of finely divided particles of carbon uniformly dispersed in a matrix of an organic polymer may be coated on a conductive layer printed on a ceramic substrate. Pace, U.S. Pat. No. 4,454,007. Although the metal conductors of Pace are somewhat shielded from contact with an analyte by a combination of a carbon layer intersolubilized with an exposed ionophoric ion-selective layer and by an insulating layer, moisture may penetrate around the ionophoric and graphite layers to directly contact and corrode the metal conductors beneath them, a corrosion problem shared with other printed electrodes. See, e.g. Hamblen et al., U.S. Pat. No. 4,053,381; Kratochvil et al., U.S. Pat. No. 4,449,011; Battaglia et al., U.S. Pat. No. 4,214,968; Kim et al., U.S. Pat. No. 4,272,328; Afromowitz et al., U.S. Pat. No. 4,133,735 Gottermeier, U.S. Pat. No. 4,273,639; Johnson et al., U.S. Pat. No. 4,020,830; Pace, U.S. Pat. No. 4,225,410; Paul et al., U.S. Pat. No. 4,184,936; Kitajuna et al., U.S. Pat. No. 4,528,085; Ho et al., U.S. Pat. No. 4,393,130; Guckel, U.S. Pat. No. 4,180,771; Blackburn, U.S. Pat. No. 4,486,292; and Blackburn, U.S. Pat. No. 4,456,522.

SUMMARY OF THE INVENTION

The present invention provides an ion-selective electrode having an electrically insulating substrate with a planar first surface substantially free of metalization thereupon, a second surface and a means for sensing a potential affixed to the first surface. A conductor passes through the substrate from the first surface to the second surface, an electrically insulating layer covers the conductor and a planar, non-metallic lead, lying between the insulating layer and substrate, except for a window of this non-metallic lead. The non-metallic lead connects the means for sensing and the conductor, with the sensing layer and any metallization on the first surface being distinctly located at a separate situs. Hereinafter, that a first element is located "at a separate situs on said first surface" with reference to a second element is intended to mean that the first element does not lie along a line normal to said first surface along which line the second element lies.

Preferably, the means for sensing includes a non-metallic, conductive termination and an exposed ion-selective membrane layer covering said termination. The electrically insulating layer preferably includes a first stratum affixed to the first surface, a second stratum intersolubilized with the membrane layer, and a third stratum covering the second stratum.

The ion-sensitive electrode according to the present invention may have means for sensing which includes a non-metallic, offset gate connected to a gate lead of a ChemFET and an exposed ion-selective membrane layer covering said offset gate.

It is a particular disadvantage of layered electrodes that placement of metal under a membrane or even under several layers, including a layer of graphite in a thermoplastic binder, permits moisture from the wet environment in which such electrodes are used to contact the metal. This problem has so hampered reuse of such electrodes that it is proposed in Pace, U.S. Pat. No. 4,454,007 a reference which describes an ion-selective electrode (employing a layer of conductive material having coated thereon a layer of carbon dispersed in dielectric polymer) that the electrodes should be disposed of after a single use.

In the present invention, metallization is not used on the surface of the device which contacts an analyte. Rather a non-metallic, conductive material forms the conductive portions of the sensing element and also forms the leads connecting a sensing element of the electrode with a conductor passing through the insulating substrate to a surface of the device, which surface is shielded from the analyte. The non-metallic conductive material may include graphite in a suitable supportive and binding matrix or may include a conductive polymer, such as polyacetylene and polypyrrole among others.

DETAILED DESCRIPTION

Figure 1:
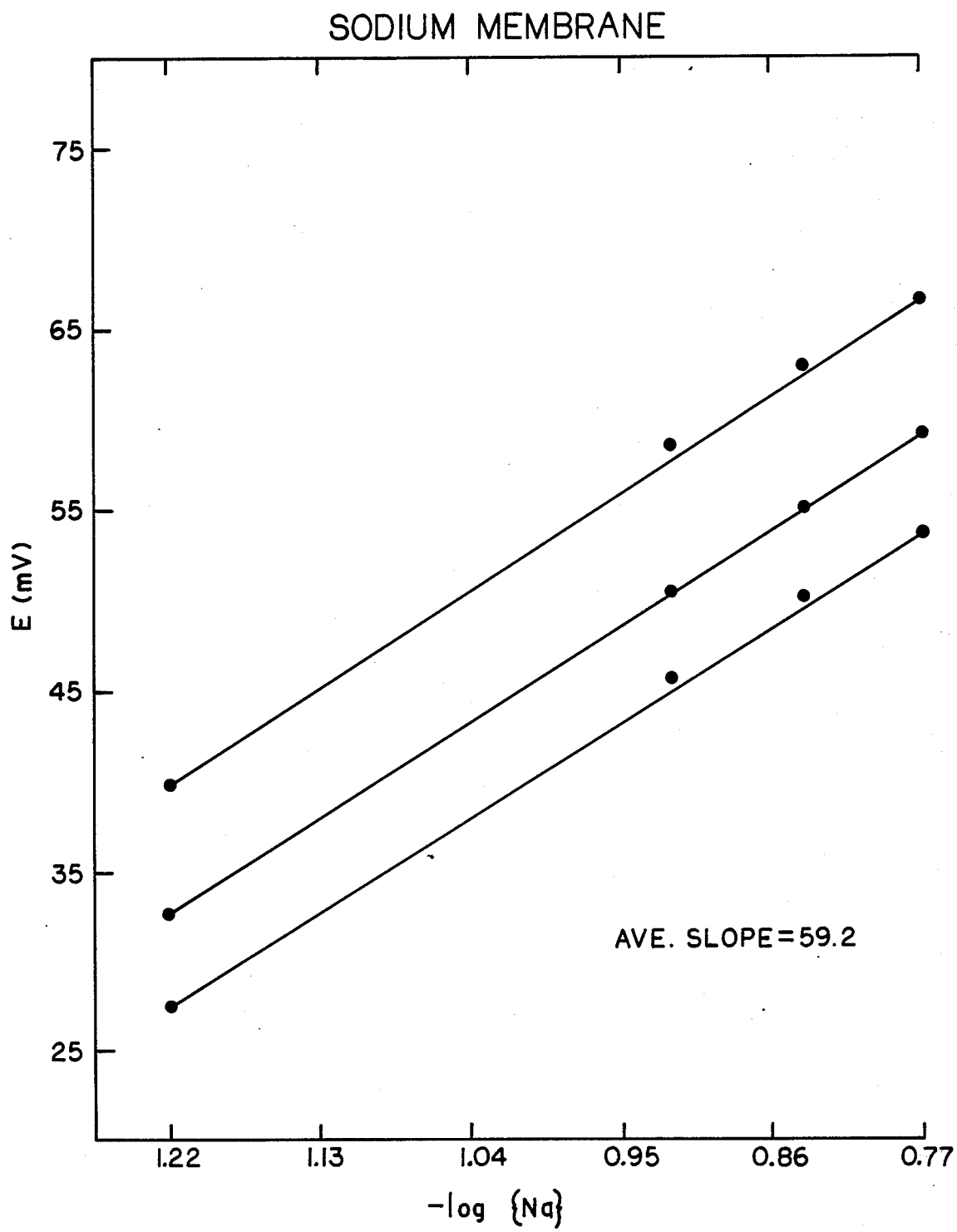
FIG. 1 is a graph of potential versus the negative of the log of sodium ion concentration for a preferred embodiment of the present invention incorporating a sodium ion-selective membrane.
Figure 2:
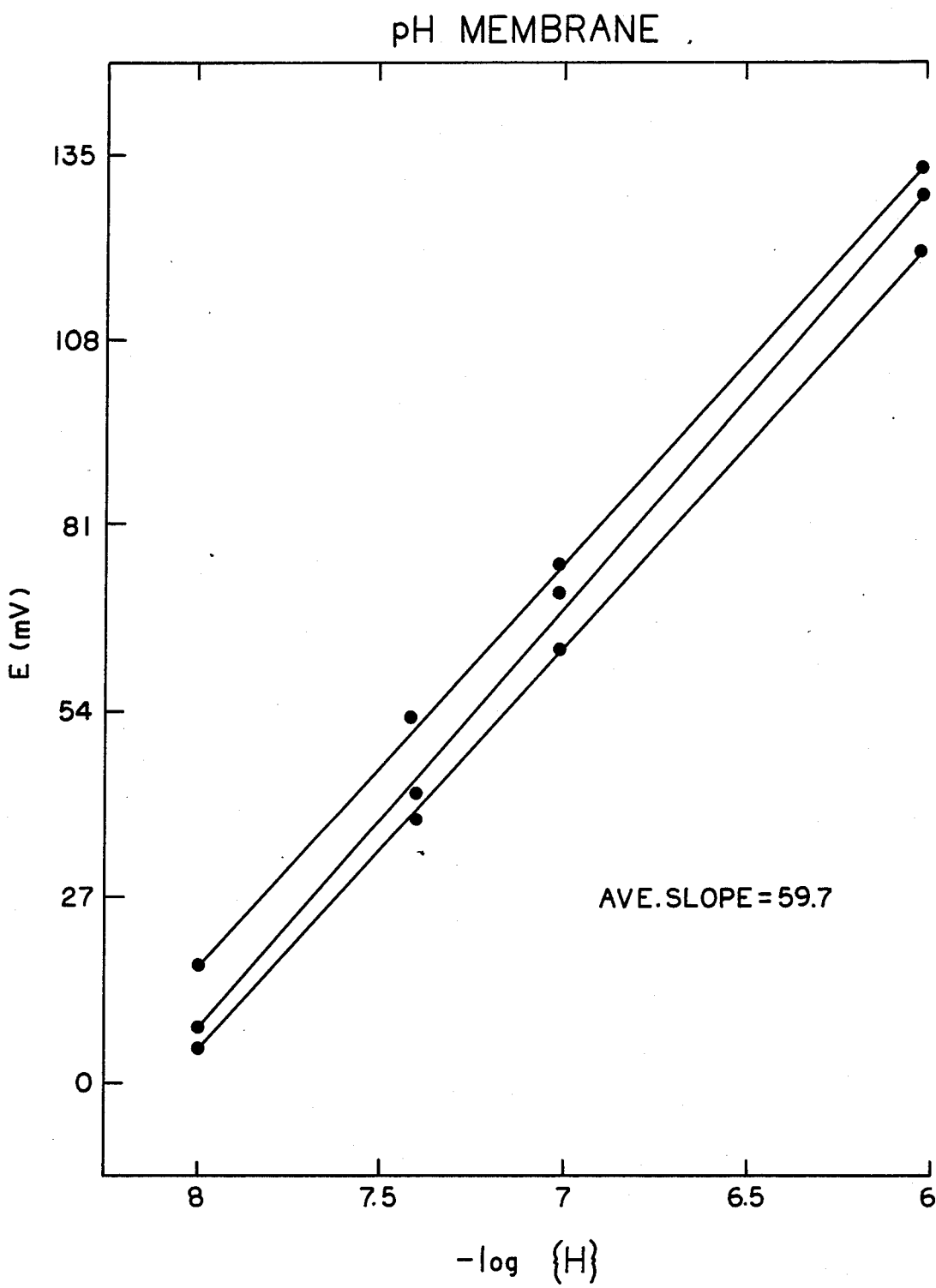
FIG. 2 is a graph of potential versus the negative of the log of pH in a preferred embodiment of the present invention incorporating a pH-selective membrane.
Figure 3:
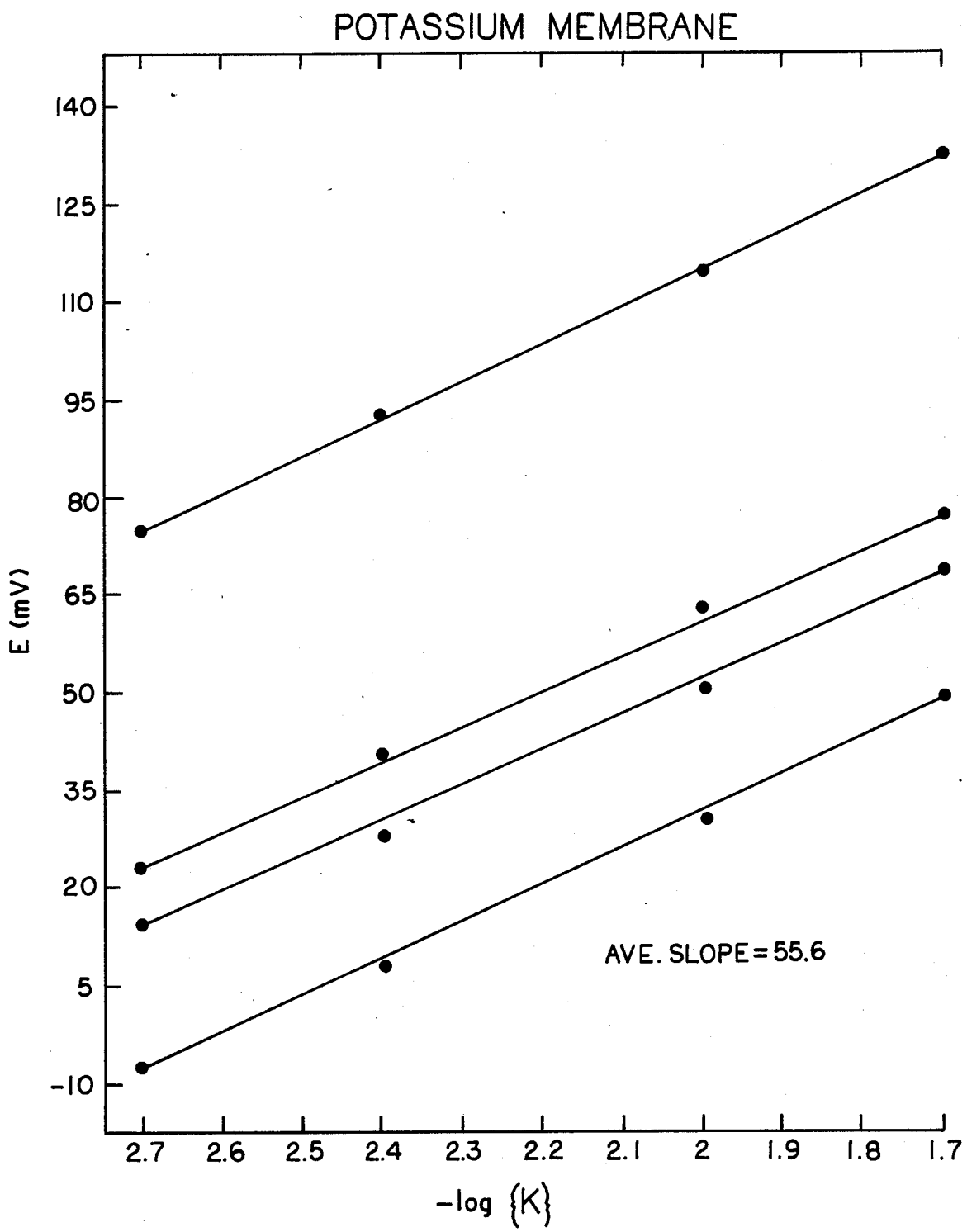
FIG. 3 is a graph of potential versus the negative of the log of potassium ion concentration in a preferred embodiment of the present invention incorporating a potassium ion selective membrane.
Figure 4:
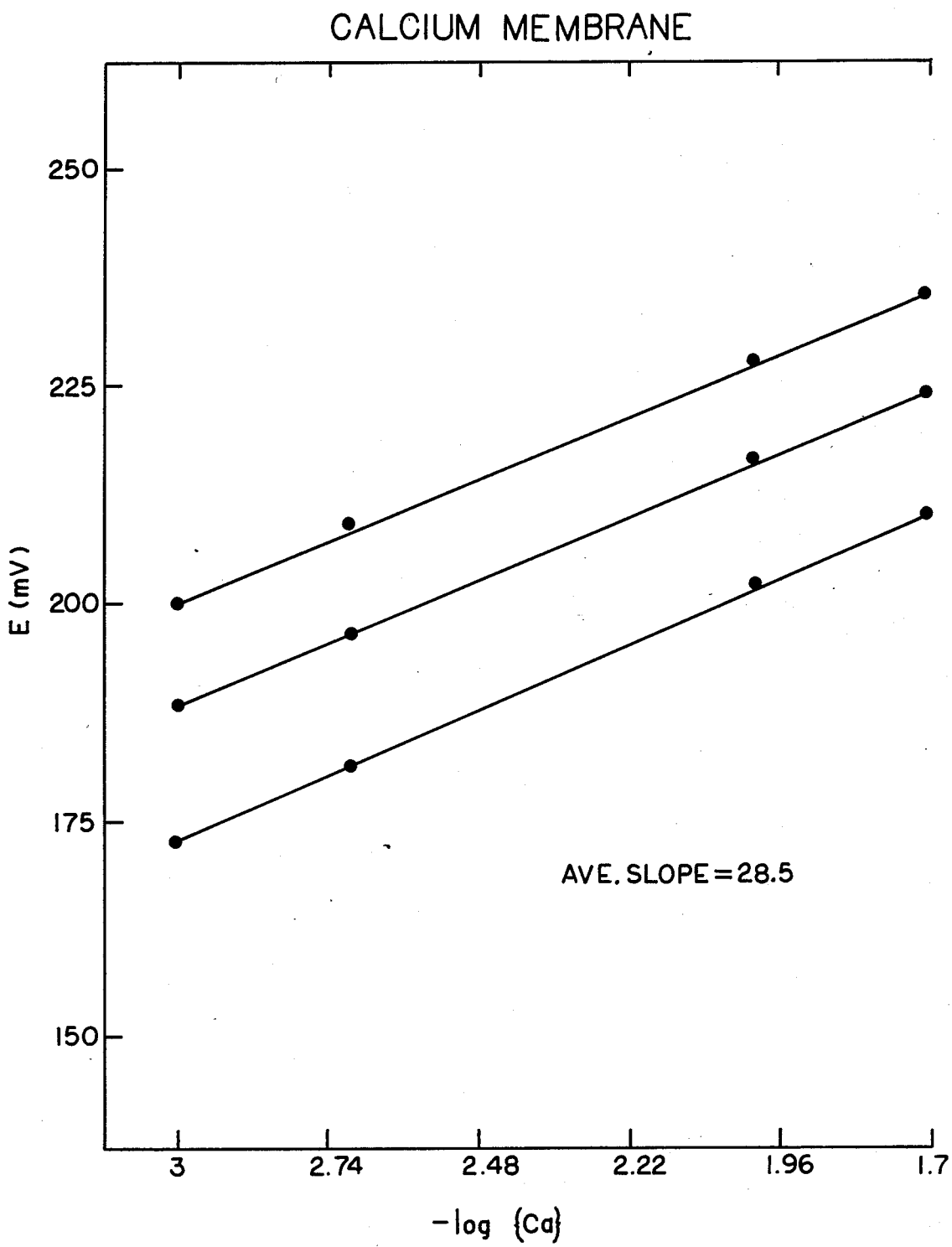
FIG. 4 is a graph of potential versus the negative of the log of calcium ion concentration in a preferred embodiment of the present invention incorporating a calcium ion selective membrane.

An electrode according to the present invention is a miniaturized, planar-coated, ion-selective electrode. Specifically an ion selective electrode is formed from a substrate having a planar first surface free of metalization at the situs for ion-detection. In one aspect, a conductor passes through the substrate to the first surface where a non-metallic lead such as conductive carbon connects the conductors to a situs where the ion-selective electrode membrane is deposited. In another aspect, a conductor on the first surface intersects a non-metallic lead, such as conductive carbon, which connects the conductor to a situs where the ion-selective electrode membrane will be deposited.

Conductive carbon such as graphite particles are dispersed in a blend of polymer and solvent. This dispersion is applied to an electrically-insulating planar surface by various processing techniques, such as thin or thick film patterning. It may also be dip or spray-coated over wires or other non-planar surfaces. The solvent is chosen to solubilize the polymer binder, so that the graphite may be uniformly dispersed. The solvent is removed from the system by drying. The polymer is chosen to adhere to the graphite particles and bind them tightly in the matrix after the solvent evaporates. The polymer is also chosen to provide intersolubilization with the polymer/solvent system of an overlying ion-selective membrane and to permit ion selectivity of the system as known in the art.

The advantages of this system include adhesion and good electrical contact between the graphite and membrane. The system may be applied in a thin or a thick film format. It may be used as an ion-selective electrode surface directly in applications where long leads are not required to connect the ion-selective electrode to a device for measuring potential. If long leads are necessary e.g. where the device is used for in vivo monitoring, the system may be applied over a gate area of a FET or between a gate contact and a sensing area.

The present invention also provides a screen-printable chemical anchor and well for containing a polymeric membrane which is specially formulated for application on a semiconductor chip or on a thin- or thick-film substrate in order to detect specific chemistries such as ions, electrolytes, metabolites, enzymes, proteins, and blood gasses.

Screen printing is used in the fabrication of thick film microelectronics such as hybrids, and is an established technique for the laydown of thixotropic electronic materials. Construction of a membrane anchor/well by screen printing simplifies physical application of the membrane, controls the geometry of the membrane, controls the thickness of the membrane, and provides physical support for the membrane. Screen printing of a membrane anchor and well permits unlimited variation in planar geometry of sensing areas without a threat to the membrane, and also permits a virtually unlimited number of sensors per device. Moreover, encapsulation and definition of sensor areas are accomplished simultaneously and cross contamination of various membranes on one device is prevented.

In addition, specific polymeric materials may be selected to provide for: chemical adherence between membrane and encapsulant or anchor; physical protection of sensing; surface and electrical integrity of substrate, chip circuitry and external electrical connections from adverse environments.

The present invention also employs a solvent-sensitive material (which may be a thermoplastic polymer) to encapsulate part of the overcoat material in a zone around the sensing areas. When implemented by screen printing, a screening pass is made after or between undercoat and overcoat passes. A solvent in the membrane formulation partially dissolves the thermoplastic material and thus provides an "anchor" for improved adhesion of the membrane. This adhesion also improves moisture resistance and eliminates leakage current failure of the coating. There is a chemical adherence between the membrane and the insulating material encapsulating the conductive areas.

A deep membrane well prevents cross contamination of the membranes and provides physical support for the membranes.

In a preferred embodiment, an insulative substrate is cleaned ultrasonically and by vapor degreasing using an appropriate solvent (such as Freon TA). The substrate is annealed at 160° C. for 90 minutes and slow cooled to room temperature. The substrate is used as a base for a screen printing pattern. The screens used consist of standard mesh materials with emulsions as known in the art. Inks for various layers are formulated to meet requirements for thick film printing. Standard screen printing apparatus are adjusted to meet the print requirements of the various inks and patterns employed.

In this embodiment graphite particles, dispersed in a suitable matrix are printed in straight line patterns on the substrate. An insulator is then spread or printed over the graphite and substrate in a pattern which forms a window or opening over an area of the graphite. In this embodiment, the insulator is printed to total thicknesses, varying from 15 to 500 microns, to define a well over the opening. The substrate and/or insulative design also permits electrical contact to the graphite pattern at some offset from the window.

To remove potential contamination (particulate, organic, etc.), the opening above the graphite is rinsed with an appropriate solvent (such as acetone, MEK or THF). After rinsing, a membrane formulated as known in the art, is applied in liquid form over the graphite surface in the well area. Approximately 0.1 microliters of the membrane formula may be applied in the well. Depending on membrane formula, multiple applications of a membrane may be used in the same well to provide the proper integrity.

As examples, some useful membrane formulas are: for $Na^+$, 140 mg dibutyl sebacate, 60 mg PVC, 1 ml THF, and 2 mg of a $Na^+$ ionophore; for pH, 20 mg tridodecylamine, 132 mg dibutyl sebacate, 1 ml THF, 51 mg PVC and 1.4 mg sodium tetraphenylborate; for $K^+$, 140 mg di-2-ethylhexyladipate, 1 ml THF, 60 mg PVC and 2.0 mg valinomycin; and for $Ca^{++}$, 41.8 mg nitrophenyloctylether, 6.6 mg PVC, 0.2 ml/THF, 4.7 mg $Ca^{++}$ ionophore, and 0.47 mg sodium tetraphenylborate. After applying the membrane, the solvent is allowed to evaporate out of the membrane. After evaporating the solvent, membranes may be conditioned in appropriate solutions as known in the art.

Various ISEs, prepared as described above, were evaluated in solutions of varying concentration for the ion of interest. The solutions during testing were kept at a constant temperature of 25° C. Electrical connection from one area of the graphite was made to a pole of a pH meter having a display readable in millivolts. The other pole of the meter was connected to a suitable reference electrode, such as a calomel electrode. The membrane area of the graphite and the reference electrode were immersed in the test solution and a millivolt reading was recorded from the meter. This millivolt reading varied with the log of the concentration of analyte in a linear fashion, as shown in FIGS. 1, 2, 3 and 4 respectively for sodium, pH, potassium and calcium membranes.

Figure 5:
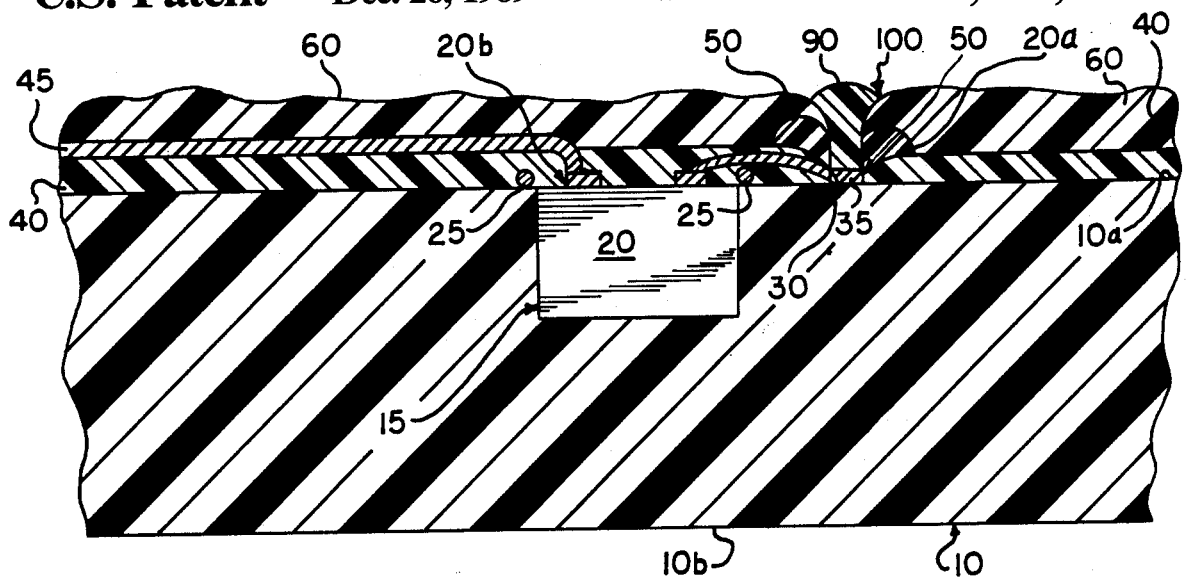
FIG. 5 is a cross-sectional view of an ion selective electrode according to the present invention having a nommetalic offset gate ChemFET.

FIG. 5 depicts an embodiment of a sensing element according to the present invention. In FIG. 5 a portion of an electrically insulating substrate 10 is shown to have a first planar surface 10a and a second planar surface 10b. As indicated in FIG. 5, surfaces 10a and 10b may respectively be an obverse and a reverse surface of a planar substrate 10. Into a depression 15 in surface 10a, a field effect transistor (FET) 20, surrounded by a screen printed insulating underring 25, is inserted substantially flush with surface 10a. A non-metallic, conductive finger 30 (preferably formed by a graphite ink) passes along the surface of the FET between a gate lead of FET 20 and a non-metallic, offset gate 35. The offset gate may be located on the FET surface or surface 10A, provided that said surface is non-metallic. Upon this construction, the rest of the sensing element is formed by layers or deposits of materials having the appropriate properties.

An electrically insulating undercoat 40 covers all portions of semiconductor 20 which is exposed at surface 10a except for an aperture 20a around an offset gate 35 and for an aperture 20b around a source lead of FET 20 and a region 20c (not shown) around a drain lead (not shown) of FET 20 and similarly for a region 20d (not shown) around a bulk lead (not shown) of FET 20. A metallic lead 45 provides an external electrical connection for the source (not shown) of FET 20. A similar metallic lead (not shown) provides an external electrical connection for the drain (not shown) of FET 20. A non-metallic conductive screen-printed lead 30 (preferably formed by a graphite ink) connects a gate lead to sensing layer 35 offset from the gate lead.

A layer 50 of an electrically insulating membrane anchor surrounds and dips down into aperture 20a to contact offset gate 35 while maintaining an aperture 20a. An electrically-insulating overcoat 60 covers the entire surface of substrate 10 except for aperture 20a. An ion-selective membrane 90 fills aperture 20a and is surrounded by a membrane well 100.

The device of FIG. 5 may be constructed as follows.

First, the substrate is annealed to remove all stress by placing it in an oven at the highest expected process temperature for 2 hours. The oven is then turned off allowing the substrate to cool to room temperature slowly. The substrate is cleaned by sonication in the presence of isopropyl alcohol and vapor degreasing with trichlorotrifluorethane. FET 20 is mounted by dispensing adhesive into substrate recess 15, and then using a vacuum tool to pick up the chip and locate it in the recess. Then the adhesive is cured according to the manufacturer's recommendations. Standard precautions are taken to avoid static shock.

An underring is screen-printed around the chip as an insulative bridge, using a screen with a mesh, angle, and emulsion as is known in the industry. An insulating ink suitable for screen printing is used and the insulating ink cured according to manufacturer's recommendations. Graphite is screen-printed as the sensing media over the gate lead on FET 20, curing the ink according to manufacturers recommendations. Insulating material 40 is next screen printed onto chip 20 and overlapping substrate 10, leaving sensor areas and contact pads uncovered. This insulating layer protects sensitive electronics of the semiconductor from adverse environments. Silver conductive runs connecting to the source and drain of FET 20 are screen-printed. Insulative overcoat material 60 is screen-printed and cured after screen printing and curing layer 50 of the membrane anchor to protect circuitry while also defining the sensing areas.

The substrate is then prepared for membrane application by rinsing sensing areas (exposed graphite) with a solvent such as trichlorotrifluoroethane, methyl ethyl ketone (MEK), or tetrahydrofuran (THF) to remove particulate matter from the surface and allowing all the remaining solvent to evaporate. The surface of the substrate is visualized with a microscope at approximately 50× magnification. An appropriate membrane formulation is applied to well 100 using a microliter syringe, onto sensing area within well 20a. The drop size is approximately 0.1 microliter. One to several drops may be applied, to obtain desired thickness of membrane 90. If multiple drops are used, each application is allowed to partially dry before the next one is applied. The membrane is cured for a period appropriate to membrane 90.

Although this embodiment retains some metallization at the surface of substrate 20 in proximity of the analyte, the membrane anchor formed by layer 50 and the minimization of metallization on surface 10a permits a longer useful life than is exhibited by devices lacking these features.

Figure 6:
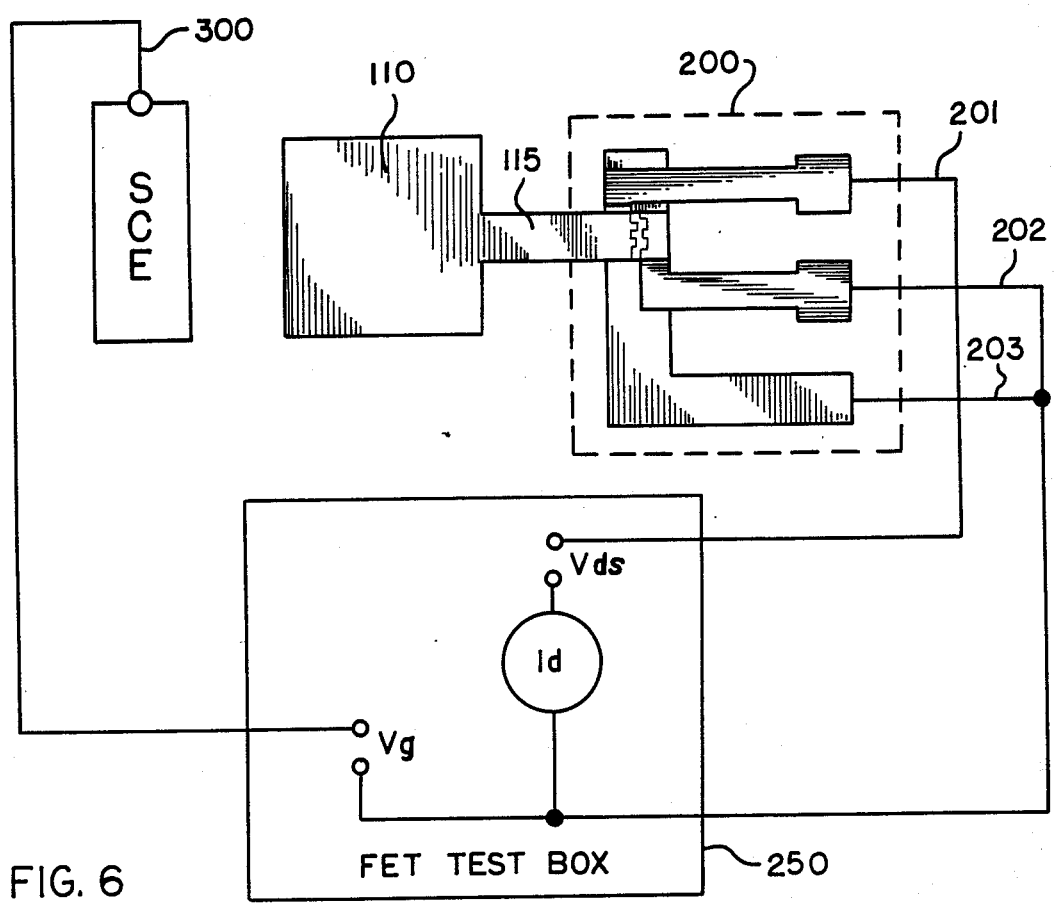
FIG. 6 is a schematic view of a preferred embodiment of an ion-selective electrode according to the present invention.

In FIG. 6, a preferred embodiment of an ion-selective electrode with a FET device according to the present invention is schematically depicted. In this device a graphite pad 110 connects a sensing area to gate 115 of FET 200. FET 200 may thus be placed away from the well in which the analyte is placed or even on the reverse surface of the substrate by connecting a FET test box to source lead 201, drain lead 202 and bulk lead 203 of FET 200 and to a standard calomel electrode 300, the device may be used as an ion-selective electrode.

The $V_{ds}$ of a FET test box 250 is set at a constant value of approximately 2 volts. The $I_d$ is fixed at a value of $-50$ microamps. The frit of electrode 300 and the membrane area over the graphite are completely immersed into a test solution. The gate voltage is read in millivolts. As the concentration of an ion changes, the potential of the membrane changes according to the Nernst equation. The FET box is configured to adjust the $V_g$ (gate voltage) proportionally to the membrane potential change, such that a constant $I_d$ is maintained. The resulting measurement $V_g$ is used in the Nernst equation as the negative equivalent of membrane potential.

The membranes useful in sensing element and FET embodiments of the present invention may be prepared as follows:

For the sensing element embodiments (i.e. those not having an active device mounted on the first surface) a $_pH$ membrane may be prepared by dissolving: 20 mg tridodecylamine (ionophore), 132 mg dibutyl sebacate (plasticizer), 51 mg polyvinyl (PVC) and 1.4 mg sodium tetraphenylboron in 1 ml tetrahydrofuran (THF).

A potassium membrane may be prepared by dissolving 2.0 mg valinomycin (ionophore), 140 mg di-2-ethylhexyl adipate (plasticizer) and 60 mg PVC in 1 ml THF.

A sodium membrane may be prepared by preparing a stock PVC/THF solution of 33.0 mg PVC in 1 ml THF and dissolving 41.8 mg o-nitrophenyl octylether (plasticizer), 1.0 mg sodium tetraphenylboron, and 4.7 mg monensin methylester (ionophore) in 0.2 ml of the stock PVC/THF solution.

For both sensing element embodiments and for FET embodiments (i.e. those having an active device mounted on the first surface), a calcium membrane may be prepared using a stock PVC/THF solution of 13.2 mg PVC in 0.4 ml THF and dissolving 41.8 mg o-nitrophenyl octylether, 0.47 mg sodium tetraphenylboron and 4.7 mg Fluka #21192 calcium ionophore in 0.2 ml of the stock PVC/THF solution.

For FET embodiments, a potassium membrane may be prepared by dissolving 41.8 mg o-nitrophenyl octylether, 0.47 mg sodium tetraphenylboron and 4.7 mg valinomycin in 0.2 ml of the same stock PVC/THF solution described for the calcium membrane.

Materials useful in the construction of ionselective electrodes as described herein may be obtained from the following sources. PVC from Polysciences Incorporated, Warrington, Pa.; THF from Aldrich Chemical Company, Milwaukee, Wis.,; sodium tetraphenylboron from Aldrich Chemical Company, Milwaukee, Wis.; dibutyl sebacate from Kodak Chemicals, Rochester, N.Y.; tridodecylamine from Kodak Chemicals, Rochester, N.Y.; valinomycin from Sigma Chemical Company, St. Louis, Mo.; di-2-ethylhexyladipate from Polysciences, Inc., Warrington, Pa.; o-nitrophenyloctylether from Fluka Chemical Corporation, Ronkonkona, N.Y.; monensin methyl ester from Calbiochem Biochemicals, San Diego, Calif. and Calcium Ionophore #21192, Fluka Chemical Corp., Ronkonkona, N.Y.

A useful substrate material for embodiments of the present invention is a thermoplastic polyester resin for injection molding available from General Electric Corporation, Albany, N.Y., as the product Valox TM 865. Screens for screen printing according to the present invention may be obtained from Microcircuit Engineering Corporation Mount Holly, N.J. as 200MESH W/1.6SS wire @ 30 degree angle using type ES emulsion. A graphite ink useful according to the present invention is available from Acheson Colloids Company, Port Huron, Mich. as product #423SS.

Figure 7:
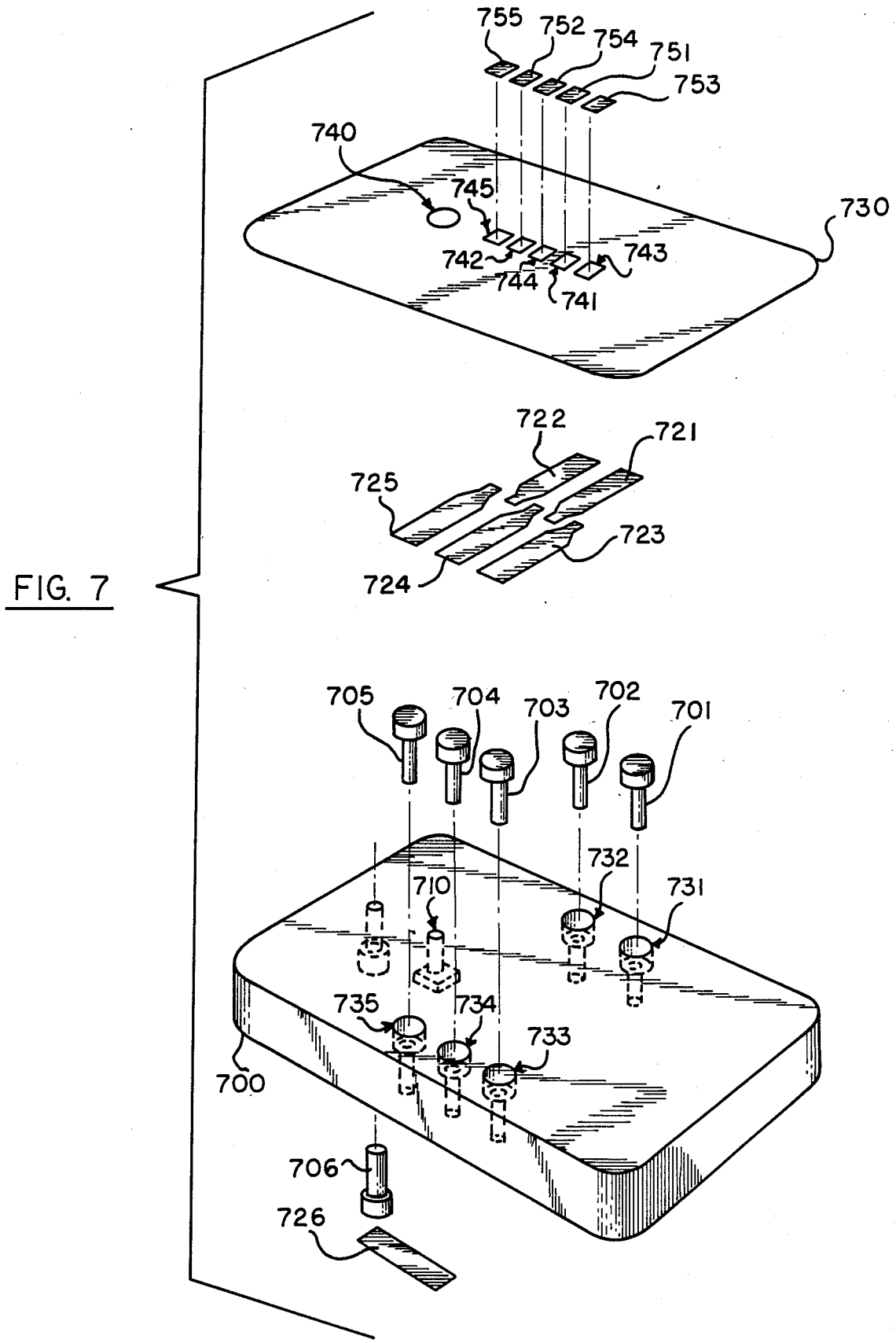
FIG. 7 is an exploded view of an ion-selective electrode according to the present invention having no electronics on the substrate.

In FIG. 7, the ion-selective electrode according to the embodiment of the present invention is illustrated. In FIG. 7, a plastic substrate 700 which holds six electrical pins (701, 702, 703, 704, 705 and 706), a reference electrode 710, five ion-selective-electrode membranes (751, 752, 753, 754 and 755), an insulating layer 730 having respective apertures 740 for reference electrode 710 and 741-745 respectively for sensing membranes 751-755, cylindrical cavities 731-735 passing through substrate 700, and conductors (721, 722, 723, 724, 725 and 726) between the pins and the reference electrode and the membranes. Reference electrode 710 is a small silver/silver chloride square. It is inserted in the bottom of substrate 700 with a potassium chloride gel above it. The gel is exposed to the test solutions via a small 0.005 inch diameter hole in the top surface of substrate 700. Conductor 726 connects from the Ag/AgCl square to conductive pin 706, on the back side of substrate 700.

The top side of substrate 700 is covered with conductive carbon traces from the pins to the area where the ion-selective-electrode membranes are placed. An insulating pattern is formed over the conductive traces to protect them. The ion-selective electrode membranes 751-755 are placed in contact with the insulating and conductive traces.

Although the present invention has been described in terms of a preferred embodiment, it is understood that variations and improvements will occur to those skilled in the art upon consideration of the present disclosure. For example, it is clear that, although a standard calomel electrode was employed as a reference electrode for testing, a reference electrode may be constructed on the substrate, for example by packing a cylindrical cavity through the substrate with a standard gel 0.1 to 0.2M in chloride ion and contacting this gel with an Ag-/AgCl electrode on the reverse side of the substrate, as described in FIG. 7.

Therefore, it is intended that the present invention include all such variations and improvements which come within the scope of the invention as claimed.

We claim:

1. An ion-selective electrode comprising:
an electrically insulating substrate having a substantially planar first surface;
a non-metallic conductor coupled to said substrate, said non-metallic conductor comprising graphite;
means, affixed to said first surface and coupled to said conductor, for sensing a potential located at a situs free of metallization, said means for sensing comprising a non-metallic conductive layer and an exposed ion-selective membrane covering said conductive layer; and
an electrically insulating layer covering a portion of said conductor, said electrically insulating layer comprising:
a first stratum affixed to said first surface;
a second stratum wherein at least a portion thereof is intersolubilized with said membrane; and
a third stratum covering said second stratum.

2. An ion-selective electrode comprising:
a substrate;
a field effect transistor on said substrate, said field effect transistor having a gate, a source, and a drain;
a non-metallic, conductive offset gate coupled to said gate of said field effect transistor, said non-metallic, conductive offset gate comprising graphite;
an exposed ion-selective membrane layer covering said offset gate; and
an electrically insulating layer covering at least a portion of said non-metallic conductive offset gate.

3. The ion-selective electrode as recited in claim 2, wherein said electrically insulating layer comprises a first stratum affixed to said substrate, a second stratum wherein at least a portion thereof is intersolubilized with said membrane layer, and a third stratum covering said second stratum.

4. An ion-selective electrode comprising:
an electrically insulating substrate having a first surface;
a metallic conductor at a first situs with respect to said substrate;
a non-metallic conductor connecting said metallic conductor to a separate situs on said first surface, said non-metallic conductor comprising graphite;
an ion-selective membrane layer covering said separate situs; and
an electrically insulating layer covering at least a portion of said non-metallic conductor.

5. The ion-selective electrode as recited in claim 4 wherein said electrically insulating layer comprises a first stratum affixed to said first surface, a second stratum wherein at least a portion thereof is intersolubilized with said membrane layer, and a third stratum covering said second stratum.

6. An ion-selective electrode comprising:
an electrically insulating substrate having a substantially planar first surface;
a non-metallic conductor coupled to said substrate;
means, affixed to said first surface and coupled to said conductor, for sensing a potential located at a situs free of metallization; and
an electrically insulating layer covering a portion of said conductor, said insulating layer forming a well above a portion of said conductor, said means for sensing a potential being provided within said well.

7. An ion-selective electrode comprising:
an electrically insulating substrate;
a field effect transistor formed on said substrate, said field effect transistor having a gate, a source, and a drain;
a non-metallic, conductive offset gate coupled to said gate of said field effect transistor;
an exposed ion-selective membrane layer covering said offset gate; and
an electrically insulating layer covering at least a portion of said non-metallic, conductive offset gate, said insulating layer forming a well above said offset gate, said ion-selective membrane layer being provided within said well.

8. An ion-selective electrode comprising:
an electrically insulating substrate having a first surface and a second surface;
a metallic conductor at a first situs with respect to said substrate;
a non-metallic conductor connecting said metallic conductor to a separate situs on said first surface of said insulating substrate, said non-metallic conductor being on said first surface of said insulating substrate;
an ion-selective membrane layer covering said separate situs; and
an electrically insulating layer covering at least a portion of said non-metallic conductor, said metallic conductor extending from said non-metallic conductor on said first surface of said insulating substrate through said insulating substrate to said second surface of said insulating substrate.

* * * * *